United States Patent [19]
Varie et al.

[11] Patent Number: 6,160,133
[45] Date of Patent: *Dec. 12, 2000

[54] SYNTHESIS OF (S)-α-METHYL-1,3-BENZODIOXOLE-5-ETHANOL AND DERIVATIVES

[75] Inventors: David L. Varie, Indianapolis; Jeffrey T. Vicenzi, Brownsburg; Milton J. Zmijewski, Carmel, all of Ind.

[73] Assignee: Eli Lilly and Company, Indianapolis, Ind.

[ * ] Notice: This patent is subject to a terminal disclaimer.

[21] Appl. No.: 09/346,795

[22] Filed: Jul. 2, 1999

Related U.S. Application Data

[62] Division of application No. 09/260,449, Mar. 2, 1999, Pat. No. 5,986,114, which is a division of application No. 08/843,307, Apr. 14, 1997, Pat. No. 5,919,954, which is a division of application No. 08/413,036, Mar. 28, 1995, Pat. No. 5,665,878, which is a continuation-in-part of application No. 08/298,645, Aug. 31, 1994, abandoned.

[51] Int. Cl.[7] .................................. C07D 317/54
[52] U.S. Cl. .......................... 549/445; 435/123
[58] Field of Search .............................. 549/445; 435/123

[56] References Cited

U.S. PATENT DOCUMENTS 4,247,560  1/1981  Mues et al. .

FOREIGN PATENT DOCUMENTS

| 0357787 | 3/1990 | European Pat. Off. . |
| 2-174683 | 7/1990 | Japan . |
| 4-234989 | 8/1992 | Japan . |
| 4-271789 | 9/1992 | Japan . |

OTHER PUBLICATIONS

Caldwell, Modern Drug Discovery, pp. 51–60, 1999.

Kim et. al., J. Org. Chem. 1993, 58, 4511–4512.

T. Lang, et al., *Chemical Abstracts*, vol. 105, No. 25, Dec. 11, 1986, abstract No. 226357v.

*Primary Examiner*—Joseph K. McKane
*Assistant Examiner*—Taofiq A. Solola
*Attorney, Agent, or Firm*—Martin A. Roy

[57] ABSTRACT

A process for stereoselectively forming N-substituted dihydro-2,3 benzodiazepines which are useful as AMPA receptor antagonists. The process includes an opening reduction step which sets the stereochemistry of the intermediates and the final compounds to the desired enantiomer. The reduction step may be carried out by an enzymatic reduction.

5 Claims, No Drawings

SYNTHESIS OF (S)-α-METHYL-1,3-BENZODIOXOLE-5-ETHANOL AND DERIVATIVES

This application is a division of application Ser. No. 09/260,449 filed on Mar. 2, 1999, now U.S. Pat. No. 5,986,114, which is a division of application Ser. No. 08/843,307 filed on Apr. 14, 1997, now U.S. Pat. No. 5,919,954, which is a division of application Ser. No. 08/413,036 filed on Mar. 28, 1995 (now U.S. Pat. No. 5,665,878), which is a continuation-in-part of application Ser. No. 08/298,645 filed Aug. 31, 1994 (now abandoned).

FIELD OF THE INVENTION

This invention relates to a novel process for synthesizing certain dihydro-2,3-benzodiazepine derivatives, and has special application to a process for producing these compounds in high enantiomeric purity and yields. It also relates to intermediates useful in the process.

BACKGROUND OF THE INVENTION

U.S. Pat. No. 4,835,152 discloses that the compound 1-(4-aminophenyl)-4-methyl-7,8-methylenedioxy-3,4-dihydro-5H-2,3-benzodiazepine possesses central nervous system effects.

European patent application publication number EP-A1-0492485 discloses 2,3-benzodiazepine derivatives and other dihydro-2,3-benzodiazepine derivatives also having central nervous system effects, in particular muscle-relaxant and anticonvulsive activity. The compounds disclosed in EP-A1-0492485 are represented by the general formula.

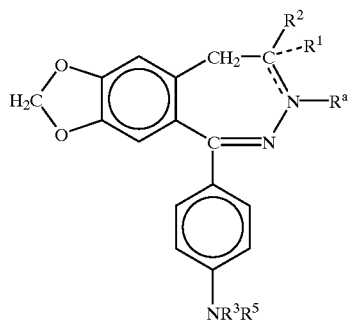

(A)

wherein $R^a$ stands for a $C_{1-6}$ aliphatic acyl group, optionally substituted by a methoxy, cyano, carboxyl, amino, $C_{1-4}$ alkylamino, di($C_{1-4}$ alkyl)amino, pyrrolidino, phthalimido or phenyl group, or by one or more halogen(s); or $R^a$ is a benzoyl, cyclopropanecarbonyl, $C_{1-5}$ alkylcarbamoyl or phenylcarbamoyl group; or $R^a$ is absent when a double bond exists between the N(3) and C(4) atoms;

$R^1$ means hydrogen; or $R^1$ is absent when a double bond exists between the N(3) and C(4) atoms;

$R^2$ means a $C_{1-3}$ alkyl group; or $R^1$ and $R^2$ together stand for a methylene group and no double bond is present between the N(3) and C(4) atoms;

$R^3$ means hydrogen or a $C_{1-4}$ aliphatic acyl group;

$R^4$ represents hydrogen; a $C_{1-6}$ aliphatic acyl group optionally substituted by a methoxy, cyano, carboxyl, amino, $C_{1-4}$ alkylamino, di($C_{1-4}$ alkyl)amino, pyrrolidino, phthalimido or phenyl group or by one or more halogen(s); as well as a benzoyl, palmitoyl, cyclopropanecarbonyl, $C_{1-5}$ alkylcarbamoyl or phenylcarbamoyl group; and the dotted lines represent valence bonds optionally being present, with the proviso that no double bond exists between the N(3) and C(4) atoms when both $R^3$ and $R^4$ stand for hydrogen.

International patent application publication number WO 92/11262 also discloses certain dihydro-2,3-benzodiazepine derivates having central nervous system effects, in particular antidepressive and/or antiparkinsonian action. The compounds may be represented by general formula (A) above in which $R^1$ represents hydrogen, $R^2$ represents methyl, $R^a$ represents hydrogen or a $C_{1-4}$ alkyl group optionally substituted by a carboxyl or $C_{2-5}$ alkoxycarbonyl group, $R^3$ represents hydrogen and $R^4$ represents an aliphatic $C_{1-6}$ acyl, benzoyl or phenylacetyl group.

It is now known that the compounds disclosed in U.S. Pat. No. 4,853,152, EP-A1-0492485 and WO 92/11262 are potent antagonists of the AMPA (α-amino-3-hydroxy-5-methylisoxazole-4-propionic acid) class of receptors in the mammalian central nervous system. They have potentially widespread applications as neuroprotective agents, particularly as anticonvulsants. Thus they may be useful in the treatment of epilepsy, cerebral ischemia, brain and spinal trauma, status seizures, Parkinson's disease and amyotrophic lateral sclerosis.

The dihydro-2,3-benzodiazepines disclosed in U.S. Pat. No. 4,835,152, EP-A1-0492485 and WO92/11262 possess a centre of asymmetry at position 4. It is now known that the (R) enantiomers, for example, (R)-7-acetyl-5-(4-aminophenyl)-8,9-dihydro-8-methyl-7H-1,3-dioxolo[4,5-h][2,3]benzodiazepine (also known as (R)-1-(4-aminophenyl)-3-acetyl-4-methyl-7,8-methylenedioxy-3,4-dihydro-5H-2,3-benzodiazepine), are more potent than the (S) enantiomers.

U.S. Pat. No. 4,835,152, EP-A1-0492485 and WO 92/11262 disclose synthetic routes for preparing the dihydro-2,3-benzodiazepines. In these routes, the dihydro-2,3-benzodiazepine ring is formed by selectively reducing a corresponding 2,3-benzodiazepine compound using an inorganic or organic-inorganic and/or complex metal hydride, such as sodium borohydride, followed if desired by separating optically active forms.

An elegant, stereoselective synthesis has now been found for preparing the (R) enantiomers of the dihydro-2,3-benzodiazepines disclosed in U.S. Pat. No. 4,835,152, EP-A1-0492485, WO 92/11262 and of certain other dihydro-2,3-benzodiazepines.

SUMMARY OF THE INVENTION

The present invention provides a process for the preparation of a compound having the general formula:

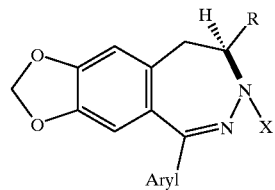

(I)

wherein R is hydrogen or $C_1$–$C_{10}$ alkyl;

X is hydrogen, $C_1$–$C_{10}$ alkyl, acyl, aryl, or carboxyl, or a substituted derivative thereof.

Novel and non-obvious intermediate compounds are formed during this process which further allow the efficient synthesis of the title compounds. Some of the novel intermediates disclosed include hemiketal and hydrazone compounds:

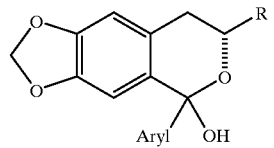

(V)

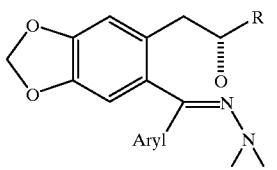

(VI)

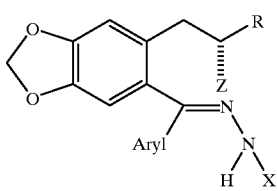

(VIII)

wherein Z represents a leaving atom or group such as a mesylate. Note that the R and X moieties retain the same meanings throughout this specification.

Accordingly, it is an object of this invention to provide for a novel stereoselective process of forming dihydro-2,3 benzodiazepine derivatives.

Another object is to provide for a process of forming dihydro-2,3 benzodiazepine derivatives which is efficient and economical, in that high yields and enantiomeric purity are obtained with fewer steps and less waste then previously disclosed.

Another object is to provide for novel intermediate compounds formed during the synthesis of dihydro-2,3-benzodiazepines.

Other objects will become apparent upon a reading of the following description.

DETAILED DESCRIPTION OF THE INVENTION

According to one aspect, the present invention provides a process for preparing a compound having the general formula:

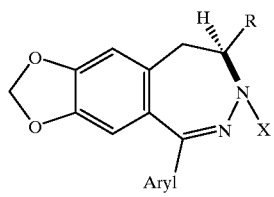

(I)

wherein R is hydrogen or a $C_1$–$C_{10}$ alkyl; and
X is hydrogen, $C_1$–$C_{10}$ alkyl, acyl, aryl, carboxyl or a substituted derivative thereof, or a protecting group, or a pharmaceutically acceptable salt thereof, said process comprising cyclising a compound having the general formula

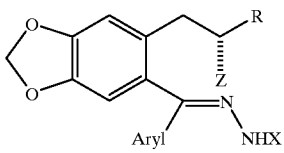

(VIII)

wherein Z represents a leaving atom or group, to afford a compound having the general formula I, whereafter, if desired, converting the compound of formula I into another compound of formula I and/or forming a pharmaceutically acceptable salt.

It has been found that compounds of formula (I) can be prepared in high yield and high enantiomeric purity by the process according to the invention.

As used herein, the term "$C_1$–$C_{10}$ alkyl" represents a straight or branched alkyl chain having from one to ten carbon atoms. Typical straight or branched $C_1$–$C_{10}$ alkyl groups include methyl, ethyl, n-propyl, isopropyl, n-butyl, isobutyl, sec-butyl, t-butyl, n-pentyl, isopentyl, n-hexyl, 2-methylpentyl, n-octyl, decyl and the like. The term "$C_1$–$C_{10}$ alkyl" includes within it the terms "$C_1$–$C_4$ alkyl" and "$C_1$–$C_6$ alkyl".

The term "aryl" represents an aromatic moiety, such as phenyl, thienyl, furyl, pyridyl, imidazolyl and polynuclear aromatic moieties, such as naphthyl, phthalazinyl, quinolyl, fluorenyl, anthracyl and phenanthrenyl. The term "substituted aryl" represents an aryl group substituted with one or more moieties chosen from the group consisting of halogen, hydroxy, cyano, nitro, $C_1$–$C_6$ alkyl, $C_1$–$C_4$ alkoxy, carboxy, acetyl, formyl, carboxymethyl, hydroxymethyl, amino, aminomethyl or trifluoromethyl. Examples of substituted aryl groups include 4-methylphenyl, 2-methylphenyl, 4-methoxyphenyl, 4-(i-propyl)phenyl, 4-cyclopentylphenyl, 4-(t-butyl)phenyl, 4-acetylphenyl, 4-trifluoromethylphenyl, 4-chlorophenyl, 2-bromophenyl, 3-iodophenyl, 6-bromonaphthyl, 3,4-(methylenedioxy)phenyl, indanyl, 1,2,3,4 tetrahydronaphthyl, and 1,2,4,4-tetramethyl-1,2,3,4-tetrahydronaphthyl.

The term "acyl" represents a hydrogen, a $C_1$–$C_6$ alkyl group or a heteroatom (for example nitrogen, as in an amido group) attached to a carbonyl group. Typical acyl groups include formyl, acetyl, propionyl, butanyl, valeryl, hexanyl, carbamoyl, N-methylcarbamoyl and ureyl.

"Aryl", used in the formulae throughout the specification, represents an unsubstituted or substituted aryl group. Examples of values for Aryl are p-nitrophenyl, p-aminophenyl and p-(protected amino)phenyl such as p-($C_1$–$C_6$ alkanoylamino)phenyl, for example p-acetylaminophenyl. Examples of suitable protecting groups may be found in McOmie, Protective Groups in Organic Chemistry, Phenum Press, N.Y. 1973, and Greene and Wutz, Protecting Groups in Organic Synthesis, 2d. ed., John Wiley and Sons, N.Y., 1991.

R preferably represents a $C_1$–$C_3$ alkyl group, for example methyl.

Examples of values for X are hydrogen, formyl, acetyl, propionyl and methylcarbamoyl.

X preferably represents a $C_1$–$C_6$ aliphatic acyl group, optionally substituted by a methoxy, cyano, carboxyl, amino, $C_1$–$C_4$ alkylamino, di($C_1$–$C_4$ alkyl)amino, pyrrolidino, phthalimido or phenyl group, or by one or more halogens); or R is benzoyl, cyclopropanecarbonyl, $C_1$–CS alkylcarbamoyl or a phenylcarbamoyl group.

The leaving atom or group represented by Z may be for example, a halogen atom or an organosulfonyloxy group, or may be generated in situ from the corresponding compound of formula VIII in which Z represents hydroxy.

Particular values for Z when it represents a halogen atom are chlorine and bromine.

An organosulfonyloxy group represented by Z may be, for example, or $C_1$–$C_4$ alkanesulfonyloxy group, a trifluoromethanesulfonyloxy group or a phenylsulfonyloxy group in which the phenyl group is unsubstituted or substituted by one or two substituents selected independently from $C_1$–$C_4$ alkyl, $C_1$–$C_4$ alkoxy, halogen, nitro and halo $C_1$–$C_4$ alkyl. Particular values for Z are methanesulfonyloxy, phenylsulfonyloxy, p-toluenesulfonyloxy and p-nitrophenylsulfonyloxy.

It has been found that a much better yield is obtained by cyclising a compound of formula VIII in which Z is an organosulfonyloxy group rather than a compound of formula VIII in which Z is a halogen atom.

When Z represents a halogen atom or an organosulfonyloxy group, the cyclisation is preferably performed in the presence of a base selected from alkali metal hydroxides, for example sodium or potassium hydroxide; alkali metal carbonates, for example sodium or potassium carbonates; alkali metal hydrides, for example sodium or potassium hydride; and alkali metal alkoxides, for example lithium, sodium or potassium t-butoxide. The process is conveniently performed at a temperature in the range of from –30 to 100° C., preferably from 0 to 50° C. Suitable solvents include alkanols such as methanol or ethanol, and ethers such as tetrahydrofuran.

A compound of formula VIII in which Z represents a leaving atom or group may be generated in situ, by reacting a for example compound of formula VIII in which Z represents a hydroxyl group with a triarylphosphine in the presence of an azidodicarboxylate ester. The reaction is analogous to the well known Mitsunobu reaction. Preferably the triarylphosphine is triphenylphosphine and the azodicarboxylate ester is diethyl azodicarboxylate. The process is conveniently performed at a temperature in the range of from –30 to 100° C., preferably from –10 to 50° C. Suitable solvents include ethers such as tetrahydrofuran. It will be appreciated that in this instance, the leaving group represented by Z is a triarylphosphonyloxy group such as triphenylphosphonyloxy.

The process according to the invention is of particular interest for preparing compounds of formula (I) in which Aryl represents p-aminophenyl. Such compounds are preferably prepared by cyclising a compound of general formula VIII in which Aryl represents p-nitrophenyl, p-aminophenyl or p-(protected amino)phenyl, whereafter, if necessary, (a) reducing a p-nitrophenyl group to afford a p-aminophenyl group, or (b) deprotecting a p-(protected amino)phenyl group to afford a p-aminophenyl group.

According to a preferred aspect, the present invention provides a process for preparing a compound having the general formula I in which R is methyl and X represents hydrogen, formyl, acetyl, propionyl or N-methylcarbamoyl or a pharmaceutically acceptable salt thereof, which comprises cyclising a compound having the general formula VIII in which R is methyl, X is hydrogen, formyl, acetyl, propionyl, N-methylcarbamoyl or a protecting group and Aryl is p-nitrophenyl, p-aminophenyl or p-(protected amino) phenyl, whereafter, if necessary;

(a) reducing a p-nitrophenyl group to afford a p-aminophenyl group;

(b) deprotecting a p-(protected amino)phenyl group to afford a p-aminophenyl group;

(c) removing a protecting group represented by X to afford a compound of formula I in which X is hydrogen; and/or (d) acylating a compound of formula I in which X is hydrogen to afford a compound of formula I in which X is formyl, acetyl, propionyl or N-methylcarbamoyl; and, if desired, forming a pharmaceutically acceptable salt.

The nitro group in a p-nitrophenyl group may be reduced by a method known in the art, for example as described in EP-A1-492485. Thus it may be reduced by reaction with hydrazine or hydrazine hydrate in the presence of Raney nickel catalyst. Alternatively, it may be reduced by reaction with hydrogen, formic acid, ammonium formate, a trialkylammonium formate such as triethylammonium formate or an alkali metal formate such as sodium formate or potassium formate, in the presence of a Group VIII metal catalyst such as palladium on charcoal. Suitable solvents include alcohols such as methanol, ethanol or isopropanol, and ethers such as tetrahydrofuran, or acetone. The reduction may conveniently be performed at a temperature in the range of from –10 to 120° C.

The protecting group in a p-(protected amino)phenyl group may be removed in a conventional way. For example, a $C_{1-6}$ alkanoyl group may be removed by hydrolysis in the presence of a mineral acid, for example hydrochloric acid.

Acylation of a compound of formula I in which X is hydrogen to afford a compound of formula I in which X is an acyl group, such as formyl, acetyl, propionyl or N-methylcarbomoyl, may be performed as described in EP-A1-492485.

The compounds of formula VIII in which Z represents a hydroxyl group or leaving atom or group are believed to be novel, and are provided as a further aspect of the invention.

The compounds of general formula VIII may be prepared by a multistep process, starting from a methylenedioxyphenyl acetone derivative.

According to another aspect, therefore, the present invention provides a process for preparing a compound having the general formula:

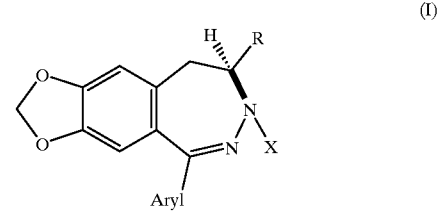

wherein R is hydrogen or $C_1$–$C_{10}$ alkyl; and

X is hydrogen, $C_1$–$C_{10}$ alkyl, acyl, aryl, carboxyl, or a substituted derivative thereof; said process comprising the steps of:

a) providing a quantity of a compound having the formula:

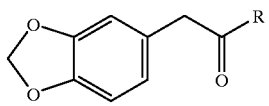

(II)

b) asymmetrically reducing the compound of formula II to yield a compound having the formula:

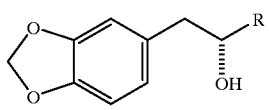

(III)

c) reacting the compound of formula III with an arylaldehyde compound of formula Aryl.CHO to yield an isochroman compound having the formula:

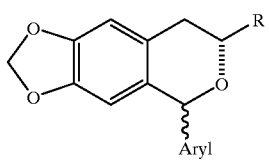

(IV)

d) reacting the compound of formula IV with an oxidizing agent to yield a compound of the formula:

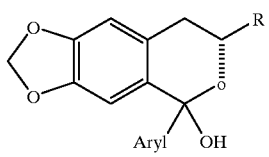

(V)

e) reacting the compound of formula V with a hydrazide derivative of formula $H_2NNHX$ to yield a compound of the formula:

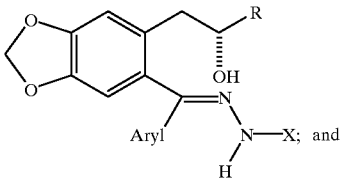

(VI)

f) reacting the compound of formula VI with a (i) sulfonyl halide reagent and a base, to form an intermediate sulfonate, followed by reacting the resultant sulfonate with a strong base; or (ii) by direct Mitsunobu cyclization to yield the compound of formula I.

The novel process of this invention provides a synthesis of fewer steps, higher yields and stereoselectivity, and generates no heavy metal and very little overall waste. The process includes an early enantioselective reduction step at which time the stereochemistry is set to the preferred isomer (in this case the (R) or (−) enantiomer for the final product).

The preferred process involves the early chiral reduction of a ketone to an alcohol. Substituents are added in a multi-step process to close the benzo-fused pyran ring, before a hydrazine reagent is introduced to open the ring and add the necessary nitrogen components. Finally, the secondary ring is closed by addition of a strong base and the compound is reduced to form the desired compound.

Most preferably, the chiral reduction step is the initial step in the synthesis of the Formula (I) compounds from ketones. The chiral reduction may be effected by use of specific chemicals or, preferably, by using biological agents as disclosed below. Setting the stereochemistry early in the process is beneficial and allows for the later steps to be carried out on relatively enantiomerically pure material. This increases both throughput and enantiomeric purity.

The first step of the process involves a chiral reduction of the starting material (preferably a 3,4-methylenedioxyphenyl acetone derivative) to produce a virtually enantiomerically pure alcohol derivative of 1,2-methylenedioxybenzene. Preferably, the enantiomer formed is the (S) or (+) stereoisomer of the alcohol. The most preferred starting compound is 3,4-methylenedioxyphenyl acetone.

Alternatively, the initial step may involve the combination of a halo derivative of 1,2-methylenedioxybenzene with an enantiomerically enriched epoxide. This also results in the production of a highly enantiomerically enriched alcohol derivative of 1,2 methylenedioxybenzene.

The material used to effect the chiral reduction initial step may be either chemical or preferably biological. In the case of biological agents, the preferred agents are reducing enzymes, most preferred being yeasts from the Zygosaccharomyces group. Other biological agents which may be used include: *Pichia fermentans, Endomycopsis fibuligera, Nematospora coryli,* Saccharomyces sp., *Candida famata, Saccharomyces pastorianus, Saccharomyces cerevisiae, Saccharomyces uvarum, Candida utilis, Saccharomyces globosus, Kluyveromyces dobzhansk, Kluyveromyces lactis, Candida albicans,* bakers' yeast, *Zygosaccharomyces rouxii, Lactobacillus acidophilus, Aureobasidium pullulans, Mortierella isabellina, Rhizopus oryzae, Kloeckeva javanica, Hanseniaspora valbyensis, Octosporomyces octospori, Candida guilliermondi, Candida parapsilosis, Candida tropicalis, Torulopsis taboadae, Torulopsis ethanolitolerans, Torulopsis ptarmiganii, Torulopsis sonorensis, Trigonopsis variabilis, Torulopsis enokii, Torulopsis methanothermo,* SAF instant yeast, ashland yeast inact., *Candida boidinii, Candida blankii* and Red Star yeast.

The desired intermediate formed in the initial step is an alcohol substituted congener of 1,2-methylenedioxybenzene, with the most preferred congener consisting of (S)-α-Methyl-1,3-benzodioxole-5-ethanol.

The desired intermediate compound formed in the initial step is then subjected to a Pictet-Spengler reaction which provides for convergent fusion of the benzodiazepine carbon constituents. The preferred reagent of choice is p-nitrobenzaldehyde, although other reagents known to those skilled in the art, such as acetals, may be used. The preferred intermediates are dihydrobenzopyrans with the most preferred compound being 7,8-dihydro-7-methyl-5-(4-nitrophenyl)-5H-1,3-dioxolo-benzo[b]pyran.

The dihydrobenzopyran congener is then oxidized at the C5 position to yield a hemiketal derivative of the general formula:

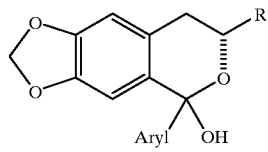

(V)

The preferred oxidizing agents include potassium permanganate, DDQ (2,3-dichloro-5,6-cyano-1,4-benzoquinone) or others, with the most preferred agent being a sodium hydroxide, dimethyl sulfoxide and air combination.

The C5-hemiketal is then reacted with a hydrazide derivative of formula $H_2NNHX$ in the presence of acid in order to form the hydrazone intermediate. In this step, the benzopyran ring is opened such that the hydrazone component becomes attached to the C5 carbon. The most preferred hydrazide is acetic hydrazide and is preferably reacted in a refluxing aromatic or protic solvent, with the preferred hydrazone being of the general formula

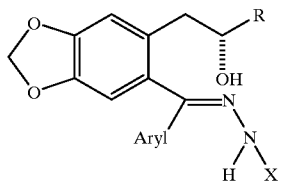

(VI)

wherein R is $CH_3$, X is acetyl and Aryl is p-nitrophenyl.

The hydrazone derivative is converted into the desired benzodiazepine ring via intramolecular alkylation. This is accomplished by one of several possible methods. The first method involves the addition of a mixture of a sulfonyl halide reagent of formula $YSO_2X^a$ in which $X^a$ represents a halogen atom such as chlorine and which Y represents an organic group such as $C_1$–$C_4$ alkyl, trifluoromethyl, or phenyl in which the phenyl group is unsubstituted or substituted by one or two substituents selected independently from $C_1$–$C_4$ alkyl, $C_1$–$C_4$ alkoxy, halogen, nitro and halo $C_1$–$C_4$ alkyl (for example, methanesulfonyl chloride) and a base, such as a tertiary amine (for example, triethylamine) to form a sulfonate intermediate of formula

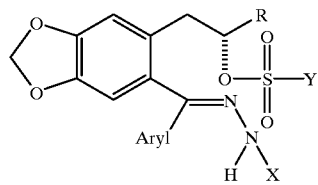

(VII)

The sulfonate is then converted to the 8,9-dihydro-7H-2,3-benzodiazepine congener by addition of a strong base, most preferably an alkali metal hydroxide such as caustic soda, an alkali metal alkoxide such as sodium or potassium tert-butoxide, an alkali metal carbonate such as potassium carbonate or an alkali metal hydride such as sodium hydride. optionally, the reaction may be performed in the presence of a phase transfer catalyst, such as tetrabutylammonium bromide.

Alternatively, the compound of formula VI may be converted into a compound of formula VIII in which z represents a halogen atom, for example, a compound of formula VI may be reacted with imidazole, triphenylphosphine and bromine to afford a compound of formula VIII in which Z represents a bromine atom. The resultant compound for formula VIII may then be cyclised following the same procedure as that used for a compound of formula VIII in which Z represents an organosulfonyloxy group.

Surprisingly it has been found that the cyclisation of a compound of formula VIII in which Z represents an organosulfonyloxy group can be performed in high yield, with remarkably little elimination. However, with a compound of formula VIII in which Z is a halogen atom, the yield is substantially lower, due to competing elimination.

Accordingly, the use of a compound of formula VIII in which Z represents an organosulfonyloxy group (corresponding with a compound of formula VII) is preferred.

Another method involves a Mitsunobu cyclization which is a one-step process to yield the p-nitrophenyl benzodiazepine intermediate.

When a compound of formula I in which Aryl represents p-aminophenyl is desired, and a compound of formula IV in which Aryl represents p-nitrophenyl has been prepared, the nitro group may be reduced at any stage in the process. Preferably it is reduced after process step e) or The nitro group may be reduced by addition of hydrogen gas or a hydrogen source in the presence of a catalyst. The preferred hydrogen source is potassium formate, or other formate salt (such as ammonium formate), with the preferred catalyst being a combination of palladium metal and activated charcoal. The reduction step is well known to those skilled in the art.

The preferred processes can be summarized by the following schemes to yield the most preferred product.

Scheme (I)

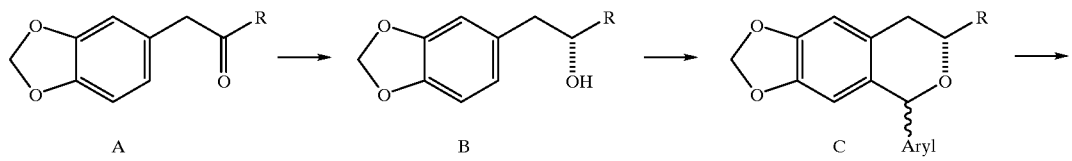

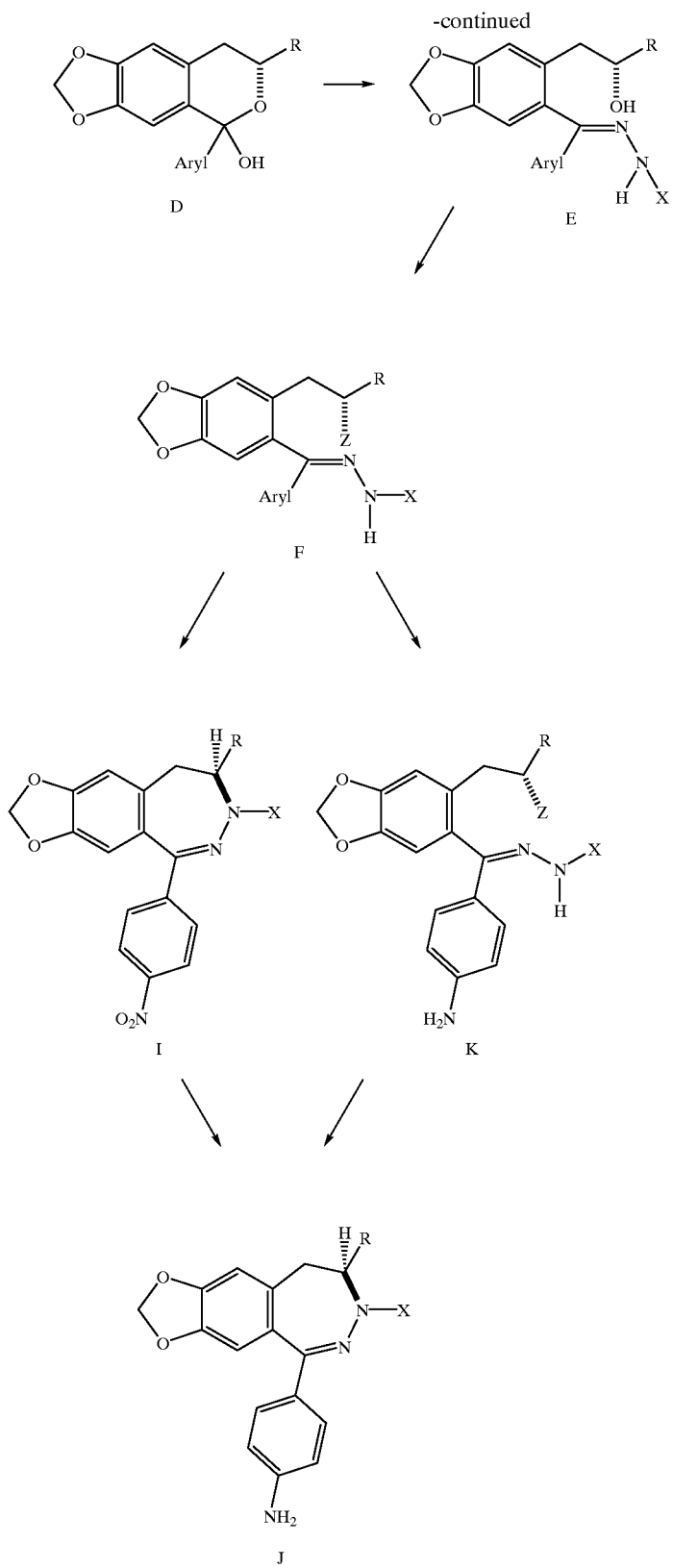
In scheme (I), the initial step of the process involves the addition of biological agents, most preferably *Zygosaccharomyces rouxii,* to reduce the ketone to the desired alcohol.
A suitable quantity of an adsorbent resin such as AD-7, XAD-7, HP2MGL (cross-linked polymethacrylates from Rohm & Haas), HP20 (polystyrenic), or SP207 (brominated polystyrene from Mitsubishi) may be added to the reaction mixture to prevent death of the organism and to adsorb the alcohol as it is formed.

Other similar resins may also be used.

SCHEME II

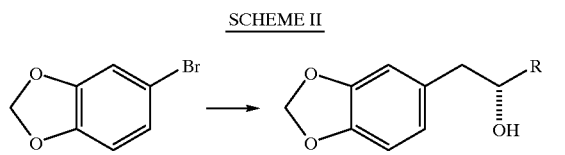

In scheme (II), the initial step of the process involves reacting an aryl halide derivative, such as 4-bromo-1,2 (methylenedioxy) benzene, with an alkali metal hydrocarbon (sec-butyllithium is preferred) and an enantiomerically pure epoxide. Preferred is (S)-(−)-propylene oxide. Alternatively, an aryl halide may first be converted into a Grignard reagent by reaction with magnesium, then reacted with an enantiomerically pure epoxide in the presence of copper(I) iodide as catalyst. In both scheme (I) and scheme (II), the objective is to set the stereochemistry of the C8 atom of the benzodiazepine ring as early as possible. Both schemes have been observed to accomplish this objective and have formed enantiomerically enriched (ee) alcohols in the 98% purity range.

The following examples are indicative of the process of this invention.

EXAMPLE 1

Synthesis of (S)-α-methyl-1,3 benzodioxole-5-ethanol 1 equiv. of 3,4-methylenedioxyphenyl acetone, 0.45 equiv. disodium phosphate, 0.03 equiv. phosphoric acid, 12.5 volumes AD-7 resin and 5.8 volumes of water were mixed together and stirred for 15–60 minutes at 20–25° C. 2.27 equiv. of glucose were added and Z. rouxii $ATCC_{14462}$ is added in an amount of 1.5 grams wet cell paste per gram of ketone (this is 0.375 grams/gram on a dry basis). This mixture was diluted with water to 25 volumes and then gently stirred at 33–35° C. for 8–16 hours. The mixture was filtered on a 100 mesh (~150 micron) stainless steel screen, and the resin which was retained by the screen was washed with 25 volumes of water split into 4 separate portions. The product, which was adsorbed to the resin, was then desorbed from the resin with 25 volumes of acetone. The acetone/product solution was then stripped to dryness under vacuum to yield the title intermediate as a yellow, medium viscosity oil. The in-situ yield was 97–100%, while the isolated yield was 85–90%. The potency was 80–95% and the EE is 100%.

EXAMPLE 2

Synthesis of (5RS,7S)-7,8 dihydro-7-methyl-5-(4-nitrophenyl)-5H-1,3 dioxolo-[4,5-G][2]benzopyran The above intermediate was dissolved in 4.64 volumes of toluene, filtered over hyflo, and washed with 1.55 volumes of toluene. 1.05 equiv. p-nitro-benzaldehyde and 1.05 equiv. of conc. hydrochloric acid were added, and the mixture was heated to 55–65° C. and stirred 1 hour. A solvent exchange was then conducted at 250 mmHg, replacing the toluene with 12.4 volumes of 93% isopropanol/7% water/ The volume during this solvent exchange varies from 11–14 volumes, and the final volume was ~11 volumes. The mixture was cooled to 0–10° C. and stirred 1 hour. The needle-like product crystals were filtered and washed 2 times with 1.85 vol. isopropanol and dried under vacuum at 50–60° C. The in-situ yield of the title compound was 95+% while the isolated yield was 87–93%. The potency was 99+% and the EE is 100%.

EXAMPLE 3

Alternative syntheses of (S)-α-methyl-1,3 benzodioxole-5-ethanol 3.47 grams of 4-bromo-1,2(methylenedioxy)benzene were dissolved in 100 ml of tetrahydrofuran at −78° C., 13.9 ml of 1.3M sec-butyllithium in cyclohexane was then added to consume the aryl halide in less than 30 minutes. 1.00 grams of (S)-(−)-propylene oxide in 2 ml THF was added by syringe and the solution stirred for 45 minutes. The solution was then warmed to 23° C. for 16 hours. The reaction mixture was poured into 3M ammonium chloride solution and the product isolated by extraction with ethyl acetate. The combined extracts were dried over magnesium sulfate filtered through florisil and concentrated by rotary evaporation. The residual oil was purified by silica gel chromatography and eluted with a 50:50 mixture of hexane and diethyl ether to yield 1.40 g (45%) of the subtitled intermediate. Pchem: $[\alpha]_{365}+117.2°$ (c 1.0, $CHCl_3$) TLC $R_f=0.26$ (50:50 hexane:ether); IR ($CHCl_3$) 3598, 3012, 2973, 2887, 1490, 1249, 1041$cm^{-1}$; $^{13}C$ NMR ($CDCl_3$) d 147.75, 146.19, 132.26, 122.27, 109.68, 108.30; mass spectrum, m/z (FD, $M^+$) 180; Anal. Calcd. for $C_{10}H_{12}O_3$: C, 66.65; H, 6.71. Found: C, 66.42; H, 6.66.

EXAMPLE 4

Alternative Synthesis of (5RS,7S)-7,8-dihydro-7-methyl-5-(4-nitrophenyl)-5H-1,3-dioxolo-[4,5-G][2]benzopyran 244 grams of p-nitrobenzaldehyde was added to a solution of 300 grams of the intermediate formed in the biocatalyzed reduction step of Example 1 in 4.45 L of toluene. 166.5 mL of concentrated hydrochloric acid was added dropwise over 15–20 min and the resulting mixture was heated to 60° C. for 2.5 h. The mixture was cooled to room temperature and concentrated by rotary evaporation. 3 L of ethanol was added and the mixture was concentrated to a solid. A second 3 L portion of ethanol was added and the mixture was stirred for 1 h. The slurry was cooled overnight and the crystalline product was isolated by vacuum filtration. The filter cake was washed with ethanol and then dried in a vacuum oven at 40–60° C. to yield 450 g (86%) of an off-white solid which was determined to be an isomeric mixture of the above subtitled optically active intermediate. P chem: $[\alpha]_{365}+55°$ (c0.4, $CHCl_3$).

EXAMPLE 5

Synthesis of (5RS,7S)-7,8-dihydro-7-methyl-5-(4-nitrophenyl)-5H-1,3-dioxolo[4,5-G ] [2]benzopyran-5-ol 350 grams of the isomeric intermediate from Example 4 was added to a solution of 731 mL of dimethylsulfoxide and 2923 mL of dimethylformamide. The mixture was cooled to 8–12° C. and compressed air was passed through the mixture. 117.5 mL of 50% aqueous sodium hydroxide was added in one portion and the resulting mixture was stirred for 4.5 h. The reaction mixture was added by cannula over 30–60 min to 8.25 L of a stirred 1N hydrochloric acid solution at 10–15° C. The resulting precipitate was filtered and washed with 3 L of water then air dried to a constant weight (384 g). The wet cake was carried into Example 6 without further drying. P chem: Data recorded from a 3:1 isomeric mixture. TLC $R_f$=0.19 (75:25 hexane:ethyl acetate); IR (CHCl$_3$) 3605, 3590, 3015, 3000, 2960, 2910, 1608, 1522, 1484, 1352, 1240, 1042cm$^{-1}$; $^1$H NMR (CDCl$_3$, 300 MHz) δ (major isomer) 8.16 (d, 2H, J=6.9 Hz), 7.73 (d, 2H, J=6.9 Hz), 6.55 (s, 1H), 6.38 (s, 1H), 5.86 (s, 1H), 5.83 (s, 1H), 4.38 (M, 1H), 2.70 (m, 2H), 1.39 (d, 3H, J=6.3 Hz); d (minor isomer) 8.27 (d, 2H, J=8.9 Hz), 7.90 (d, 2H, J=8.6 Hz), 6.87 (s, 1H), 6.73 (s, 1H), 6.03 (s, 1H), 6.02 (s, 1H), 3.95 (m, 1H), 2.7 (obscured, m, 2H), 1.24 (d, 3H, J=6.1 Hz); mass spectrum, m/z (FD, M$^+$) 329; Anal. Calcd. for $C_{17}H_{15}NO_6$: C, 62.01; H, 4.59; N, 4.25. found C, 62.22, H, 4.79; N, 4.29.

EXAMPLE 6

Synthesis of (S)-acetic acid-[[6-(2-hydroxypropyl)-1,3-benzodioxol-5-yl](4-nitrophenyl)methylene] hydrazide To 350 g of the wet cake from Example 5 in 2300 mL ethanol was added 94.5 g of acetic hydrazide and 1 mL of concentrated hydrochloric acid. The resulting solution was heated to reflux for 2.5 h. The mixture was cooled to room temperature and concentrated to a yellow foam by rotary evaporation. The concentrate was dissolved in 4.9 L of ethyl acetate and washed with 1.5 L of saturated sodium bicarbonate then 1.5 L of brine. The organic phase was dried over sodium sulfate, filtered and concentrated to give 373 g of a yellow foam (91%). The material was identified as a 1:1 inseparable mixture of isomers of the subtitled compound (97% pure by HPLC). P chem: Data recorded from a 1:1 isomeric mixture. mp 167.8–169.7° C.; TLC $R_f$=0.55 (ethyl acetate); IR (CHCl$_3$) 3590, 3485, 3310, 1694, 1673, 1520, 1485, 1346cm$^{-1}$; $^1$H NMR (CDCl$_3$, 300 MHz) δ 8.64, 8.50 (s, 1H, NH), 8.18 (d, 2H, Ar—H), 7.74, 7.71 (d, 2H, J=8, Ar—H), 6.99, 6.95 (s, 1H, Ar—H), 6.52, 6.50 (s, 1H, Ar—H), 6.06, 6.05 (d, 2H, J=5, O$_2$CH$_2$), 2.44 (s, 3H, CH$_3$), 3.87 (m, 1H, CH), 2.4–2.2 (m, 2H, CH$_2$), 1.12, 1.10 (d, 3H, CH$_3$); $^{13}$C NMR (CHCl$_3$, 75 MHz) d 209.94 (C), 173.38, 173.43 (C), 149.38, 149.62 (C), 148.31, 148.58 (C), 147.90, 148.18 (C), 147.54 (C), 142.5, 143.04 (C), 132.64 (C), 127.53, 127.61 (CH), 123.75, 123.77 (CH), 122.86, 123.27 (C), 112.13 (CH), 110.55 (CH), 108.03, 108.10 (CH), 108.03, 108.10 (CH), 101.83 (CH$_2$), 67.51, 68.08 (CH), 42.37, 42.97 (CH$_2$), 23.48, 23.83 (CH$_3$), 23.48, 23.83 (CH$_3$), 20.47, 20.55 (CH$_3$); $[a]_{589}$+103.8° (c 1, CHCl$_3$); mass spectrum, m/z (FD, M$^+$) 385; Anal. Calcd. for $C_{19}H_{19}N_3O_6$: C, 59.22; H, 4.97; N, 10.90. Found: C, 58.99; H, 5.04; N, 10.68.

EXAMPLE 7

Synthesis of (S)-acetic acid[[6-[2-[(methylsufonyl)oxy]propyl]-1,3-benzodioxol-5-yl](4-nitrophenyl)methylene]hydrazide 340 grams of the Example 6 intermediate was dissolved in 2380 mL of methylene chloride. The solution was cooled to 0° to −10° C. and 187 mL of triethylamine was added. 78.2 mL of methanesulfonyl chloride was then added and the resulting mixture was stirred for 15–30 min. 510 mL of water was added. The isolated organic phase was washed with 460 mL of a 1N hydrochloric acid solution and then 500 mL of brine. The methylene choride solution was warmed to 35–45° C. and 4760 mL of hexane was added over 90 min. The mixture was slowly cooled to room temperature and then cooled further to 0–5° C. The product was isolated by vacuum filtration and dried in a vacuum oven at 40–50° C. to give 356.2 grams (87%) of an isomeric mixture of the subtitled compound as a yellow solid. P chem: Data Recorded from a 3:1 isomeric mixture. mp 150.5–152.5° C.; TLC $R_f$=0.80 and 0.73 (ethyl acetate); IR (CHCl$_3$) 1696, 1520, 1486, 1346, 1175, 1041, 923 cm$^{-1}$; $^1$H NMR (CHCl$_3$, 300 MHz) 67 8.44 (S, 1H, NH), 8.20 (d, 2H, J=8.8 Hz, Ar—H), 7.73 (d, 2H, J=8.6 Hz), 6.94 (d, 1H, J=2.7 Hz, Ar—H), 6.57 (d, 1H, 2.6 Hz, Ar—H) 6.08 (d, 2H, J=5.4 Hz), 4.77 (m, 1H, CH), 2.90 (s, 3H, SCH$_3$, major), 2.83 (s, 3H, SCH$_3$, minor), 2.66–2.57 (m, 2H, CH$_2$), 1.30 (d, 3H, CH$_3$, minor), 1.26 (d, 3H, CH$_3$, major); mass spectrum, m/z (FD, M$^+$) 385; Anal. Calcd. for $C_{20}H_{21}N3O_8S$: C, 51.83; H, 4.57; N, 9.07; S, 6.92. Found: C, 52.05; H, 4.53; N, 8.84; S, 6.96.

EXAMPLE 8

Synthesis of (R)-7-acetyl-8,9-dihydro-8-methyl-5-(4-nitrophenyl)-7H-1,3-dioxolo[4,5-h][2,3] benzodiazepine 325 g of the Example 7 intermediate was dissolved in 3174 mL methanol. To the stirred solution was added 38.1 mL of 50% caustic soda solution. The resulting mixture was stirred for 4 h. 6348 mL of water was added to the mixture and the contents were stirred for 3 h after which period the resulting precipitate was isolated by vacuum filtration. The material was dried in a vacuum oven at 45–55° C. to give 255 grams (97%) of the subtitled compound which was 97.6% pure by HPLC area %. 221 grams of the dried material was further purified by reslurry in 1105 mL of ethanol which was heated to reflux. The resulting mixture was cooled to room temperature and the precipitate was isolated by vacuum filtration. The isolate was dried in a vacuum oven at 45–55° C. to give 199 grams (90%) of the subtitled compound which was 100% pure by HPLC potency assay.

EXAMPLE 9

Synthesis of (R)-7-acetyl-5-(4-aminophenyl)-8,9-dihydro-8-methyl-7H-1,3-dioxolo[4,5h][2,3] benzodiazepine To 5 grams of the Example 8 intermediate in 50 mL of ethanol was added 0.5 grams of 10% Pd/C wetted with water. The agitated slurry was treated with a solution of 4 grams of potassium formate in 4 mL of water. The resulting mixture was stirred for 2.5 h and then filtered over Hyflo. The filtrate was concentrated to 10–20 mL by distillation and 22 mL of water was slowly added to the warm (78°) solution. The resulting mixture was heated to 90° C. and then slowly cooled to room temperature. The product was isolated by vacuum filtration and washed with 10–20 mL of water. The isolated solid was dried under vacuum at 50° C. to give 4.17 grams (93%) of the subtitled final compound which was 100% pure by HPLC potency assay. $[α]_{365}$=−303.7 (c=1,methanol)

EXAMPLE 10

Synthesis of (5RS. 7S)-7,8-dihydro-7-methyl-5-(4-nitrophenyl)-5H-1,3-dioxolo[4,5-G][2]benzopyran-5-ol 15 grams of the Example 4 intermediate (derived from the Z. rouxii-mediated ketone reduction) was dissolved in a solution of 75 mL of dimethylsulfoxide and 75 mL of dimethylformamide. The solution was cooled to 7–9° C. and then aereated with 40% oxygen in nitrogen. 7.62 grams of 50% sodium hydroxide in water was added and the resulting mixture was stirred for 3–4 h. The reation was terminated and while maintaining the temperature ≦12° C., 120 mL of toluene was added followed by a mixture of 45 mL of water and 10 mL hydrochloric acid. The phases were separated and the organic layer was washed with 75 mL of a 10% aqueous sodium thiosulfate solution. The organic layer containing the subtitled intermediate was carried into the next step.

EXAMPLE 11

Synthesis of (S)-acetic acid-[[6-(2-hydroxypropyl)-1,3-benzodioxol-5-yl](4-nitrophenyl) methylenelhydrazide To the toluene solution of the Example 10 intermediate was added 4.26 grams acetic hydrazide and (0.01 volumes) hydrochloric acid. The resulting mixture was heated to reflux for 3.5 h with removal of water by a Dean-Stark trap. The reaction mixture was concentrated by vacuum distillation to 1 volume. The concentrate was diluted with 105 mL of methylene chloride and washed with 50–55 mL each of saturated sodium bicarbonate solution and brine. The organic solution was dried over magnesium sulfate (0.25 wt. %) and filtered over a hyflo cake. The filter was rinsed with 1 volume of methylene chloride. The combined organic phase containing the subtitled intermediate was carried into the next step.

EXAMPLE 12

Synthesis of (S)-acetic acid[[6-[2-[(methylsufonyl) oxy]propyl]-1,3-benzodioxol-5-yl] (4-nitrophenyl) methylene]hydrazide The methylene chloride solution containing the Example 11 intermediate was cooled to 0 to −5° C. and 10 mL of triethylamine was added. 4.1 mL of methanesulfonyl chloride was added slowly to maintain a reaction temperature ≦0° C. 1.5 volumes of water was added to the resulting solution. The organic phase was separated and washed with 2.5 volumes of 1N hydrochloric acid solution. The organic phase was isolated and concentrated to half the original volume by atmospheric distillation. The product was precipitated by the dropwise addition of heptane (2:1 volume heptane to organic concentrate) to the solution at 45° C. The stirred mixture was cooled to 20–25° C. for 1 h, then cooled to 0 to −5° C. for 1–2 h. The precipitate was isolated by vacuum filtration and washed with 3 volumes of 4:1 heptane: methylene chloride then dried in a vacuum oven at 45–50° C. 17.43 grams of the subtitled intermediate (78%) was obtained as an optically active mixture of hydrazone isomers which was 97.7% pure by HPLC potency assay.

EXAMPLE 13

Synthesis of (R)-7-acetyl-8,9-dihydro-8-methyl-5-(4-nitrophenyl)-7H-1,3-dioxolo[4,5-H][2,3] benzodiazepine 17.5 grams of the Example 12 intermediate was suspended in 175 mL ethyl alcohol. To the stirred mixture was added 1.7 grams of powdered sodium hydroxide. The resulting mixture was stirred for 1 h. 88 mL of water was added to the mixture and the contents were stirred for 1 h after which period the resulting precipitate was isolated by vacuum filtration and washed with 175 mL of water. The material was dried in a vacuum oven at 70° C. to give 12.2 grams (86%) of the subtitled compound which was 99.9% pure by HPLC potency assay.

EXAMPLE 14

Synthesis of (R)-7-acetyl-5-(4-aminophenyl)-8,9-dihydro-8-methyl-7H-1,3-dioxolo[4,5-h][2,3] benzodiazepine Using the product of Example 13, the title compound was prepared by an experimental procedure the same as that described in Example 9.

EXAMPLE 15

(R)-7-Acetyl-8,9-dihydro-8-methyl-5-(4-nitrophenyl)-7H-1,3-dioxolo[4,5-h][2,3] benzodiazepine 1.05 grams (S)-Acetic acid [[6-[2-[hydroxy]propyl]-1,3-benzodioxol-5-yl](4-nitrophenyl)methylene]hydrazide and 0.78 grams triphenylphosphine in 70 mL tetrahydrofuran were cooled to 0° C. 0.57 grams diethyl azodicarboxylate in 5 mL tetrahydro-furan was added dropwise over 15 min. The resulting mixture was stirred for 2 h then warmed to room temperature for 2 h. The mixture was transferred to a separatory funnel and the solution was washed with 1N HCl, water and brine. The organic phase was dried over magnesium sulfate, filtered and concentrated by rotary evaporation. The residue was eluted through a silica gel column (1:1 ethyl acetate:hexane). Fractions containing the desired compound were concentrated to a yellow oil which solidified on standing. The yellow crystalline material was slurried in 30 mL of $CH_2Cl_2$ and hexane (3:7) at 0° C. The precipitate was removed by filtration and the filtrate was concentrated to a yellow foam. The residue was suspended in 10 mL ethanol which was warmed to reflux then slowly cooled to room temperature. The precipitate was collected by filtration and dried in a vacuum oven at 60° C. to give 0.51 grams (50%) of the subtitled product (100% ee) which was 98.3% pure by HPLC potency assay.

EXAMPLE 16–18

0.5 ml of frozen yeast suspension containing the microorganism of Table 1 was added to 50 ml of a yeast-malt medium in a 250 ml flask. After 48 hours of shaking, 1.0 ml of culture is added to an additional 50 ml of medium and shaken for 48 more hours. 3,4-methylenedioxyphenyl acetone is added until the final concentration is 10 grams/liter along with 1 ml of 10% glucose. The cultures are incubated and shaken for 24 hours, then analyzed by HPLC for presence of the chiral alcohol intermediate of Example 1.

TABLE 1

| Ex. # | Micro organism | Source | | % Conversion | % EE |
|---|---|---|---|---|---|
| 16 | Candida famata | (C.f.) | A.T.C.C. 26418 | 0.0 | — |
| 17 | Zygosaccharomyces rouxii | (Z.r.) | A.T.C.C. 14462 | 77.8 | 99.5 |
| 13 | Mortierrela isobellina | (M.i.) | N.R.R.L. 1557 | 1.7 | 94.3 |

EXAMPLE 19

Synthesis of (S)-acetic acid [[6-[2-[methylsulfonyl) oxy]propyl-1,3-benzodioxol-5-yl](4-aminophenyl) methylene]hydrazide To a suspension of the Example 7 intermediate (5.00 g) in 100 mL iso-propyl alcohol was added 10% Pd/C (1 g)

followed by potassium formate (3.7 g) dissolved in 8 mL water. A second portion of potassium formate (3.7 g) was added after 1.5 h which was followed by addition of 10% Pd/C (1 g). The starting material was consumed within 30 min. The mixture was filtered through a pad of diatomaceous earth and concentrated. The residue was dissolved in methylene chloride and washed with water and brine. The organic solution was dried over $Na_2SO_4$, filtered and concentrated. The title compound (4.52 g) was isolated as a light yellow solid in 97% yield as a 1:1.3 isomeric mixture.

Data Recorded from a 1:1.3 isomeric mixture. TLC $R_f$=0.83 (acetonitrile); IR ($CHCl_3$) 3010, 1670, 1628, 1332, 1174, 1041, 922 cm$^{-1}$; $^1$H NMR ($CDCl_3$, 300 MHz) d 8.18 (d, 2H, J=9.2), 7.39 (d, 2H, J=11.4), 7.38 (d, 2H, J=10), 6.91 (s, 1H), 6.89 (s, 1H), 6.62 (d, 2H, J=8.5), 6.61 (d, 2H, J=8.1), 6.57 (s, 1H), 6.56 (s, 1H), 6.06 (m, 4H), 4.71 (sext., 2H, J=7), 3.9 (br s, 4H), 2.86 (s, 3H), 2.78 (s, 3H), 2.74–2.49 (m, 4H), 1.29 (d, 3H, J=10.8), 1.25 (d, 3H, 10.8); mass spectrum, m/z (FD, M$^+$) 433; UV max (ethanol) 326 nm ($\epsilon$ 20767), 231 (17587), 205 (42765).

EXAMPLE 20

Synthesis of (R)-7-acetyl-5-(4-aminophenyl)-8,9-dihydro-8-methyl-7H-1,3-dioxolo[4,5-][2,3]benzodiazepine To a solution of the Example 19 intermediate 0.51 g in 6 mL THF was added a single portion of lithium tert-butoxide (0.17 g). The solution was stirred at ambient temperature for 2 h, then warmed to 40–50° C. for 4 h. The reaction was quenched by addition of 10 mL of 3M ammonium chloride. The resulting mixture was diluted with 15 mL ether and washed with 15 mL each of water and brine. The organic solution was dried over $Na_2SO_4$, filtered and concentrated. The residue was dissolved in 5–10 mL of warm methylene chloride and the product precipitated by addition of 10–20 mL of ether. The product was isolated by filtration, redissolved in ethyl alcohol and concentrated. The title compound (0.23 g) was isolated in 58% yield and 100% ee (HPLC chiral assay).

EXAMPLE 21

Methyl Semicarbazide

Into 200 mL of ethanol, cooled to 2.5° C. under a nitrogen blanket, was dissolved 17 mL (350.4 mmol) of hydrazine monohydrate. To this cold, stirring solution was added dropwise over 2 h a solution of 10.3 mL (174.6 mmol) of methylisocyanate in 150 mL of toluene maintaining the internal temperature <6° C. The clear, colorless solution was stirred for 30 min. at 5–10° C. then evaporated and dried under vacuum to afford 15.19 g of white solids. The solids were stirred in 40 mL of toluene and heated to reflux to provide a cloudy solution. After slowly cooling to room temperature and stirring for 2 h, the suspension was filtered through coarse glass. The solids were washed with hexanes and dried under vacuum at 50° C. to provide 13.39 g (86.4%) of the title compound as a white crystalline solid, mp=116° C. MS (FD+)=89. IR:3362, 3303, 1630, 1561 cm$^{-1}$. $^1$H NMR (DMSO): δ 2.57 (d, 3, J=4), 4.06 (br. s, 2), 6.27 (br. s, 1), 6.94 (br. s, 1). $^{13}$C NMR (DMSO): δ 160.87, 25.89.

EXAMPLE 22

Synthesis of (S)-2-[[6-(2-hydroxypropyl)-1,3-benzodioxol-5-yl](4-nitrophenyl)methylene]-N-methylhydrazine carboxamide In a nitrogen blanketed flask was dissolved 5.17 g (15.70 mmol) of the intermediate of Example 5 in 30 mL of ethanol.

To this stirring solution was added 1.75 g (19.7 mmol) of methyl semicarbazide. The mixture was heated to reflux to dissolve the solids and then 5 drops of conc. HCl was added. Over 1 h at reflux, yellow solids precipitated out of solution. After 1 h, HPLC analysis indicated complete reaction, 38.2% and 55.4% of 2 product isomers and no remaining starting material. The yellow slurry was slowly cooled to ambient temperature to stir for 1 h and then stirred for 30 min. in an ice water bath. The mixture was filtered through coarse glass. The solids were washed with ethanol and dried under vacuum at 50° C. to afford 5.08 g (81.2%) of the title compound as a yellow solid, mp=238° C. HPLC assay indicated two isomers, 46.2% +53.1%. MS (FD+)=400. IR: 1692, 1345 cm$^{-1}$. $^1$H NMR (DMSO): δ 0.90 (t, 3, J=6); 2.22 (m, 2); 2.72 (d, 3, J=5); 3.63 (m, 1); 4.42 (d, 1/2, J=6); 4.58 (d, 1/2, J=6); 6.10 (s,2); 6.69 (d, 1, J=8); 7.05 (d, 1, J=10); 7.32 (br. t, 1, J=4); 7.85 (d, 2, J=9); 8.18 (d, 2, J=9); 8.62 (d, 1, J=8). $^{13}$C NMR (DMSO) δ 24.27, 24.51, 27.18, 43.30, 43.73, 67.09, 67.47, 102.45, 108.95, 109.19, 111.50, 111.54, 112.41, 112.45, 124.40, 124.48, 124.69, 128.35, 133.47, 133.69, 144.55, 144.61, 144.68, 144.79, 147.71, 147.76, 148.06, 149.39, 149.54, 156.11, 156.23. Anal. Calcd for: $C_{19}H_{20}N_4O_6$: C, 57.00; H, 5.03; N, 13.99; Found: C, 57.72; H, 5.01; N, 13.99.

EXAMPLE 23

Synthesis of (S)-N-methyl-2-[[6-[2-[-(methylsulfonyl)oxy]propyl]-1,3-benzodioxol-5-yl] (4-nitrophenyl)methylene]hydrazine carboxamide In a nitrogen blanketed flask was slurried 2.00 g (5.00 mmol) of the Example 22 intermediate in 120 mL of dry THF. The mixture was heated slightly to dissolve the solids then slowly cooled back to ambient temperature without precipitation. To the yellow solution was added 1.1 mL (7.89 mmol) of triethylamine. The solution was then cooled in an ice water/NaCl bath and 500 μL (6.34 mmol) of methanesulfonyl choride was added. After 30 min, HPLC showed complete reaction, 99.0% mesylate. The reaction was quenched with 50 mL of water and transferred to a separatory funnel with 100 mL of ethyl acetate. The organic layer was washed with 1N HCl (50 mL) and brine (50 mL) then dried ($Na_2SO_4$). The solvent was evaporated to afford 2.56 g of crude title compound as a yellow solid/foam. The crude title compound was dissolved in 12 mL of $CH_2Cl_2$ and the solution was heated to reflux. To the solution was added 6 mL of hexanes dropwise inducing precipitation of yellow solids. The mixture was slowly cooled to ambient temperature while stirring. After 1 h at ambient temperature, the mixture was filtered through coarse glass and the solids washed with hexanes. After drying at 50° C. and 30" Hg, the title compound was collected as 2.19 g (91.6%) of yellow crystals, mp=164° C. MS (FD)=478. IR: 1696, 1346 cm$^{-1}$. $^1$H NMR (DMSO): δ 1.12 & 1.19 (d, 3, J=6); 2.52 (m, 2); 2.73 (d, 3, J=3); 2.98 & 3.03 (s, 3); 4.76 & 4.84 (q, 1, J=6, 12); 6.13 (s, 2); 6.74 & 6.78 (s, 1); 7.16 & 7.20 (s, 1); 7.33 (br t, 1, J=5); 7.86 (d, 2, J=9); 8.18 & 8.22 (d, 2, J=9); 8.76 (s, 1). $^{13}$C NMR (DMSO) 67 21.35, 21.47, 27.09, 38.55, 79.50, 79.91, 102.56, 109.34, 109.46, 111.34, 111.37, 111.72, 111.74, 124.37, 124.42, 124.86, 128.26, 128.36, 130.01, 130.14, 143.74, 143.81, 144.22, 144.32, 147.93, 147.98, 148.19, 148.25, 149.65, 155.97. Anal. Calcd for: $C_{20}H_{22}N_4O_8S$: C, 50.21; H, 4.63; N, 11.71: Found: C, 50.46; H, 4.71; N, 11.65.

EXAMPLE 24

Synthesis of (R)-7-N-methylcarbamoyl-8,9-dihydro-8-methyl-5-(4-nitrophenyl)-7H-1,3-dioxolo[4.5-h][2,3]benzodiazepine In a nitrogen blanketed flask was slurried 1.50 g of the Example 23 intermediate in 40 mL of dry THF. The stirring, yellow mixture was cooled in an acetone/ice bath and 276 mg (3.45 mmol) of lithium t-butoxide was added. After stirring for 1 h, HPLC analysis of the cloudy, orange/red mixture indicated 96.5% of the desired compound and only 3.1% remaining starting material. After 90 min. the reaction was quenched with 5 mL of saturated aqueous $NH_4Cl$ and the mixture was transferred to a separatory funnel with 5 mL $H_2O$ and 60 mL of $CH_2Cl_2$. The yellow organic layer was washed with 20 mL of 1N HCl, saturated aqueous $NaHCO_3$, and brine then dried over $Na_2SO_4$. The solvent was removed by evaporation to afford 1.29 g of crude title compound as a yellow solid/foam. MS (FD+)=382.2; Anal. Calcd for $C_{19}H_{18}N_4O_5$: C, 59.68; H, 4.74; N, 14.65; Found: C, 60.00; H, 5.13; N, 13.75.

EXAMPLE 25

Synthesis of (R)-5-(4-aminophenyl)-8,9-dihydro-8-methyl-7-N-methylcarbamoyl-7H-1,3-dioxolo[4.5-h][2,3]benzodiazepine In a nitrogen blanketed flask was dissolved 902 mg (2.36 mmol) of the Example 24 intermediate in 9 mL of ethanol. To this solution was added 90 mg of 10% Pd/C followed by a solution of 690 mg (8.20 mmol) of potassium formate in 0.7 mL of water. The formate solution was added via pipette over about 30 seconds and initiated an exotherm which reached 53° C. after 2–3 min. After 15 min. HPLC analysis of an aliquot of the reaction mixture indicated only the desired product. The black reaction mixture was filtered through an ethanol wetted pad of celite over microfibre paper and the filter was washed with copious ethanol. The filtrate was evaporated to afford 953 mg of crude title compound as light, yellow solids. After attempted recrystallization from aqueous ethanol, the material was partitioned between water and ethyl acetate. The organic layer was washed with brine and dried over $Na_2SO_4$. The solvent was evaporated and ethanol stripped from the product several times to afford 647 mg (97%) of the title compound as a light tan to yellow solid, mp=142.4° C. Chiral HPLC assay determined 99.50% ee.

EXAMPLE 26

Synthesis of (S)-acetic acid [[6-(2-bromopropyl)-1,3-benzodioxol-5-yl](4-nitrophenyl)methylene]hydrazide 1.0 g (2.59 mmol) of the Example 6 intermediate, 0.265 g (3.89 mmol) of imidazole, and 0.849 g (3.24 mmol) of triphenylphosphine were combined in 10 mL of $CH_2Cl_2$ at ambient temperature producing a golden yellow solution which was cooled to 0° C. in an ice water bath. After cooling to 0° C., 0.414 g (2.59 mmol) of bromine was added. The resulting solution was stirred for 90 min at 0° C. during which time it was observed to become slightly cloudy. The reaction was then quenched by the addition of 6 mL of 1N HCl. The mixture was transferred to a separatory funnel where it was washed twice with 20 mL of 1N HCl followed by washing with 10 mL of a saturated brine solution. The organic solution was dried over $Na_2SO_4$, and evaporated to a reddish-brown, gummy solid. Chromatography on flash silica gel using 2:1 ethyl acetate/hexanes afforded 0.71 g (78%) of the title compound. About 5% of the styrene from elimination of the bromine was present as a contamiment. A mixture of hydrazone double bond isomers and amide rotomers was observed which complicated the $^1H$ NMR spectrum. $^1H$ NMR ($CDCl_3$) 1.39, and 1.44, and 1.58, and 1.65 (d, 3, J=6), 2.48 (s, 3), 2.50–2.85 (m, 2), 3.85–4.15 (m, 1), 6.09 (s, 1), 6.11 (s, 1), 6.55 (s, 1), 6.94(s, 1), 7.73 and 7.80 (d, 2, J=9 ), 8.19, and 8.20 (d, 2, J=9), 8.37, and 8.45 (s, 1). $MS(FD^+)M^+$=450 observed for $C_{19}H_{18}N_3O_5Br$.

EXAMPLE 27

Synthesis of 7-acetyl-8,9-dihydro-8-methyl-5-(4-nitrophenyl)-7H-1,3-dioxolo[4.5-H][2,3]-benzodiazepine 0.100 g (0.22 mmol) of the Example 26 intermediate was dissolved in 2 mL of dry THF and cooled to 0° C. in an ice water bath under a blanket of nitrogen. 0.018 g (0.22 mmol) of lithium t-butoxide was then added. The mixture was stirred at 0° C. for 2 h during which time the progress of the reaction was monitored via HPLC. Since HPLC revealed that approximately 10% of product had formed and a substantial amount of starting material still remained, the flask was capped with a glass stopper and placed in a freezer at −35° C. for 3 days. After an additional 8 h at room temperature, HPLC indicated 16% desired product. The reaction mixture was quenched with 1 mL of a 50% saturated aqueous $NH_4Cl$ solution and transferred to a separatory funnel with 10 mL of $CH_2Cl_2$. The mixture was washed twice with 10 mL of 1N HCl followed by 10 mL of a saturated brine solution. The organic solution was dried over $Na_2SO_4$, and evaporated to a yellow-brown gummy solid. Yield 0.05 grams. The desired product was formed in about 15% yield as judged by comparison of the $^1H$ NMR spectrum and HPLC trace with those of authentic product. The major product resulted from elimination to the corresponding styrene derivative.

EXAMPLE 28

Alternative synthesis of (S)-α-methyl-1,3-benzodioxole-5-ethanol

To a suspension of magnesium turnings (17 g) in 50 mL tetrahydrofuran was added dropwise a solution of 5-bromo-1,3-benzodioxole (93.6 g). After complete addition, the mixture was diluted with 250 mL tetrahydrofuran and the resulting mixture was stirred overnight. 13 mL of the solution (0.78 M) was transferred to a round bottom flask containing copper(I) iodide (0.12 g). The resulting mixture was cooled to −50° C. and a solution of (s)-(−)-propylene oxide in 3 mL tetrahydrofuran was slowly added then stirred 10 min. The mixture was diluted with ether. The isolated organic phase was washed with water and brine. The aqueous wash was extracted with ether (2×) and the combined organic solutions were dried over magnesium sulfate, filtered and concentrated. The residue was purified by silica gel chromatography (50% ether in pentane) to give 1.66 g of the desired product (91%). Chiral HPLC analysis indicated that the optical purity of the material was 98.3%.

EXAMPLE 29

Synthesis of (R)-7-acetyl-8,9-dihydro-8-methyl-5-(4-nitrophenyl)-7H-1,3-dioxolo[4,5-h][2,3]benzodiazepine To a suspension of the Example 7 intermediate (1.53 g) in 60 mL toluene was added 10 mL 1N sodium hydroxide and tetrabutylammonium bromide (0.053 g). The resulting mixture was stirred vigorously for 72 h. The mixture was washed with brine and the organic phase was dried over magnesium sulfate, filtered and concentrated by rotary evaporation. The residue was dissolved in ethanol and concentrated to dryness to give 1.05 of the title compound (86%). HPLC analysis indicated that <0.5% of the corresponding elimination product was generated.

What is claimed is:

1. (S)-α-Methyl-1,3-benzodioxole-5-ethanol.

2. A process for preparing a compound of the general formula:

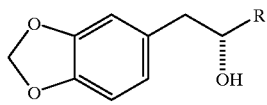
III wherein R is H or $C_1$–$C_{10}$ alkyl; comprising the steps of:

a) providing a quantity of a compound having the formula:

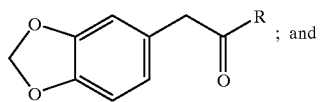
II
; and b) asymmetrically reducing the formula II compound by adding a microorganism thereto to form the compound of formula III.

3. The process of claim 2 wherein step (b) further includes adding an adsorption resin to the formula II compound.

4. The process of claim 2 wherein R is —$CH_3$.

5. The process of claim 2 wherein said microorganism is *Candida famata*, *Zygosaccharomyces rouxii*, *Mortierrela isobellina* or *Candida guilliermondi*.

* * * * *